United States Patent
Tai et al.

(10) Patent No.: US 7,683,207 B2
(45) Date of Patent: Mar. 23, 2010

(54) PURIFICATION OF N-(PHOSPHONOMETHYL)GLYCINE

(75) Inventors: Jimmy Jui Tai, Midland, MI (US); Herbert Nathan Praay, Midland, MI (US); James William Ringer, Midland, MI (US); Mark Victor Michael Emonds, Midland, MI (US)

(73) Assignee: Dow AgroSciences LLC, Indianapolis, IN (US)

( * ) Notice: Subject to any disclaimer, the term of this patent is extended or adjusted under 35 U.S.C. 154(b) by 731 days.

(21) Appl. No.: 11/133,739

(22) Filed: May 20, 2005

(65) Prior Publication Data
US 2006/0264655 A1 Nov. 23, 2006

Related U.S. Application Data

(60) Provisional application No. 60/573,255, filed on May 21, 2004.

(51) Int. Cl.
*C07F 9/22* (2006.01)
(52) U.S. Cl. .......................................... 562/11; 562/17
(58) Field of Classification Search .................. 562/11, 562/17
See application file for complete search history.

(56) References Cited

U.S. PATENT DOCUMENTS 3,799,758 A 3/1974 Franz et al.
3,956,370 A 5/1976 Parry et al.
5,859,289 A * 1/1999 Miyata et al. .................. 562/17
6,660,878 B2 * 12/2003 Wulff et al. .................. 558/386
2005/0035060 A1 * 2/2005 Vigil et al. .................... 210/639

FOREIGN PATENT DOCUMENTS

WO WO 03/000704 1/2003

OTHER PUBLICATIONS

International Search Report for PCT/US2005/017989, Nov. 14, 2005, Dow AgroSciences LLC [Jimmy Jui Tai, et al.].
International Preliminary Report on Patentability for PCT/US2005/017989, Apr. 12, 2006, Dow AgroSciences LLC [Jimmy Jui Tai, et al.].

* cited by examiner

*Primary Examiner*—Daniel M Sullivan
*Assistant Examiner*—Chukwuma O Nwaonicha
(74) *Attorney, Agent, or Firm*—Craig E. Mixan

(57) ABSTRACT

The present invention is a process for the purification of glyphosate (PMG) comprising:
1) dissolving or suspending a material comprising PMG in water, in the presence of a base, to produce a composition comprising a PMG salt in an aqueous base,
2) contacting the composition with an acid, such that the PMG salt is neutralized, forming a precipitate of PMG, and
3) isolating the precipitate of PMG,
with the proviso that the composition of step 1) is not concentrated or filtered using a nanofiltration membrane.

10 Claims, No Drawings

PURIFICATION OF N-(PHOSPHONOMETHYL)GLYCINE

CROSS REFERENCES TO RELATED APPLICATIONS

This application claims the benefit of the U.S. Provisional Application No. 60/573,255 filed May 21, 2004.

The present invention relates to the purification of N-(phosphonomethyl)glycine, commonly referred to as glyphosate or PMG.

The synthesis of glyphosate (PMG) can be achieved by a number of known routes, including by catalytic oxidation of N-(phosphonomethyl)iminodiacetic acid (PMIDA) and hydrolysis of glyphosate triester. However, the various reactions which lead to PMG production and the starting materials utilized, produce various by-products and contaminants in the final PMG product, including glycine, iminodiacetic acid (IDA), N-formylglyphosate, N-(phosphonomethyl)iminodiacetic acid (PMIDA), (aminomethyl)phosphonic acid (AMPA), N-methyl-N-(phosphonomethyl)glycine (Me-PMG), N,N-bis(phosphonomethyl)amine (bPMNH, or iminobis(methylenephosphonic acid)), N,N-bis(phosphonomethyl)glycine (bPMG or glyphosine) and sodium chloride (NaCl).

Well over 250,000 metric tons of glyphosate are sold annually. The production costs, including costs of starting materials, time, energy requirements, purification, waste management, and of course product yield, are highly important in the current competitive market. Therefore, the current market for PMG requires the offering of a highly pure product under desirable economic conditions.

U.S. Pat. Nos. 3,799,758 and 3,956,370 disclose methods of preparing glyphosate. However, no analysis of impurities is presented and no further methods of purification are disclosed. WO 2003000704 discloses a process of recovering N-(phosphonomethyl)glycine (PMG or glyphosate) comprising, adjusting the pH of a liquor comprising N-(phosphonomethyl)glycine and impurities including sodium Cl/ammonium Cl, concentrating in a pressure cell nanofiltration membrane, and recovering pure N-(phosphonomethyl)glycine from the retentate by precipitation with HCl at a pH of 1.3. However, this method removes halogenide salts, and is cumbersome and expensive, by including a nanofiltration step within the purification.

Therefore, there is a continuing need for an improved method to purify PMG considering efficiency and economics, and to provide quantities of sufficiently pure PMG suitable for commercialization via large scale production.

The present invention is a process for the purification of glyphosate (PMG) comprising:

1) dissolving or suspending a material comprising PMG in water, in the presence of a base, to produce a composition comprising a PMG salt in an aqueous base, 2) contacting the composition with an acid, such that the PMG salt is neutralized, forming a precipitate of PMG, and 3) isolating the precipitate of PMG, with the proviso that the composition of step 1) is not concentrated or filtered using a nanofiltration membrane.

This method substantially removes contaminants, especially glycine and glyphosine and produces PMG of high purity while remaining economically feasible for commercial processes.

In general, the present invention is directed to a process of purifying N-(phosphonomethyl)glycine or glyphosate (referred to herein as "PMG"). PMG can be prepared in a number of different ways, such as described in U.S. Pat. Nos. 3,799,758 and 3,956,370, which are incorporated herein by reference. Such methods include esterification of glycine followed by phosphonomethylation and hydrolysis, however the glyphosate produced may include unacceptable levels of glycine and glyphosine impurities.

The process of the present invention is found to specifically reduce the amount of glycine and glyphosine in such compositions in a commercially economical way, such that the level of impurities is reduced.

The PMG material which is to be purified can be any PMG material which contains impurities in unacceptable amounts. Typically, the PMG material will contain glycine in an amount of greater than 0.1 weight percent, based on the total weight of the PMG material. Additionally, the PMG material to be purified will typically contain glyphosine in an amount of greater than 0.2 weight percent, based on the total weight of the PMG material. In general the PMG material contains at least 90 weight percent PMG technical, preferably at least 93 weight percent, based on the total weight of the PMG material.

To purify the PMG material, it is first dissolved or suspended in water and treated with base; or alternatively, it can be dissolved or suspended directly in an aqueous base such that the PMG is partially or completely converted to a more soluble salt, forming a PMG salt composition. This can be accomplished by mixing PMG material with water, followed by the addition of a base, or by mixing the PMG material with an aqueous base directly. Typically, the amount of PMG salt within the composition is such that the composition is saturated or nearly saturated. In particular, the PMG salt composition may be a slurry at ambient temperatures, but form a clear solution when heated to elevated temperatures. In some cases, some portion of the PMG may remain undissolved within the PMG salt composition. Generally, the amount of PMG (present as PMG salt or undissolved PMG material) will be from 10, preferably from 12 and most preferably from 15 to 30, preferably to 28 and most preferably to 25 weight percent based on the total weight of the PMG salt composition.

The base utilized in the process of the present invention may be any base that will form a salt of PMG which is more soluble in water than the PMG material. Typical bases include sodium hydroxide, potassium hydroxide, sodium carbonate, potassium carbonate, ammonia or ammonium hydroxide and the like.

The amount of base needed in order to provide the desired base concentration and to produce sufficient PMG salt is typically from 0.50, preferably from 0.65, and most preferably from 0.75 to 1.2, preferably to 1.1 and most preferably to 1.0 molar equivalents of base, based on the amount of PMG material. One molar equivalent of base refers to one mole of base per mole of PMG material for a monovalent base such as sodium hydroxide, or 0.5 mole of base per mole of PMG material for a divalent base such as sodium carbonate.

The composition of PMG salt in aqueous base will typically have a pH of from 1.7 to 3.5.

To aid in the dissolving process and in the formation of PMG salts, the solution can be heated so as to expedite the dissolving process and obtain a saturated or nearly saturated solution. Typically the solution is heated to a temperature of from 50 up to 85° C.

This process can also be performed at temperatures as low as 15° C. although lower temperature reduces the solubility of the PMG salt.

The composition of PMG salt in aqueous base is not further concentrated, and it is not processed through a nanofiltration membrane. Surprisingly, it has been discovered that the process of the present invention adequately removes the impurities of interest without the use of nanofiltration.

After the desired composition of PMG in aqueous base has been obtained, an acid is added to neutralize the PMG salt. Any acid which will lower the pH of the composition and achieve complete neutralization of the PMG salt can be utilized. Typical acids include any acid strong enough to completely protonate the PMG salt, such as hydrochloric acid, sulfuric acid or phosphoric acid. Hydrochloric acid and sulfuric acid are preferred due to their low cost and high aqueous solubility of their salts.

The amount of acid utilized in the neutralization is an amount which will preferably completely neutralize the PMG salt and result in precipitation of PMG. Typically the amount of acid in moles will be approximately equal to the amount of molar equivalents of base, used previously. This will typically range from 0.5, preferably from 0.6 and most preferably from 0.7 to 1.3, preferably to 1.2 and most preferably to 1.1 equivalents of acid, based on the amount of PMG material initially utilized.

Typically, the amount of acid utilized in the process of the present invention is an amount which will lower the pH of the composition to a level of from 0.3, preferably from 0.35 and most preferably from 0.38 to 1.6, preferably to 1.5 and most preferably to 1.4. The pH of the endpoint is dependent upon the temperature of the neutralization, since higher temperatures will increase the amount of PMG in solution, and the degree of dissociation of the PMG acid will increase, thereby lowering the pH.

The neutralization typically occurs at a temperature between 20 and 90° C. The acid is typically added at a slow rate or drop wise, with agitation or stirring, in order to prevent overheating of the solution.

The pH of the final solution will change as the temperature of the solution reaches room temperature or approximately 25° C. The final pH will typically be in the range of from 0.9, preferably from 1 and most preferably from 1.05 to 2.9, preferably to 1.4 and most preferably to 1.25.

The final PMG product can be recovered by any process, and is typically recovered by centrifugation, belt filtration, or vacuum filtration as is well known in the art. The product can also be optionally washed with additional water. The process of the present invention also contemplates processes including recycling steps, such as recycling of the filtrate.

The purified PMG product typically contains less than 0.1 wt. percent glycine, preferably less than 0.08 and most preferably less than 0.06 wt. percent, based on the total weight of the purified PMG. Additionally, the purified PMG product typically contains less than 0.2 wt. percent glyphosine, preferably less than 0.15, more preferably less than 0.10 and most preferably less than 0.08 wt. percent, based on the total weight of the purified PMG. The purified PMG product typically contains less than 0.1 wt. percent MePMG, preferably less than 0.08 and most preferably less than 0.06 wt. percent, based on the total weight of the purified PMG. Preferably, the purified PMG product comprises at least 95 weight percent PMG technical, more preferably at least 98 weight percent, even more preferably at least 98.5 percent and most preferably at least 99 weight percent, based on the total weight of purified PMG.

The following examples are provided to illustrate the present invention. The examples are not intended to limit the scope of the present invention and they should not be so interpreted. Amounts are in weight parts or weight percentages unless otherwise indicated.

EXAMPLE 1

A two liter, bottom drained, cylindrical, jacketed, glass vessel was equipped with an overhead electric agitator, water condenser, thermal well, pH probe, and a chemical addition tube. To the vessel was added: 200.00 g glyphosate (96.5 percent assay, with 0.11 percent glycine, 0.19 percent MePMG, and 1.00 percent glyphosine) and 800.5 g deionized water. The mixture was stirred at 245 RPM using a pitched, four blade, two tiered, glass agitator. After 15 minutes, the pH was observed to be 1.96 with internal temperature at 24° C., and addition of 89.96 g sodium hydroxide solution (0.95 molar equivalents of a 50 percent by weight aqueous solution) was commenced. The base was added over one hour utilizing a peristaltic pump. At the end of the addition, the pH was 3.57 and the solution was observed to be almost clear and colorless, although a small amount of undissolved glyphosate left the solution appearing slightly hazy. The mixture was heated to 85° C., over 45 minutes. At 85° C. the solution was now clear, colorless and a pH of 3.11 was observed. Concentrated hydrochloric acid (109.2 g of 37.5 percent HCl, 0.95 molar equivalents) was added over 45 min. The pH dropped to 0.67 and a slurry of white solids appeared. Cooling was commenced and once the internal temperature reached 30° C., the bath set point was set to 25° C. and the slurry was stirred for an additional 30 min. After the 30 min digestion, the pH was observed to be 1.66 with the internal temp being 28° C. Concentrated hydrochloric acid was added via a pipette until a pH of 1.40 was observed (3.44 g of 37.5 percent hydrochloric acid was required, 0.03 molar equivalent). The slurry was now allowed to stir and digest for two hours with the bath still at 25° C. Solid glyphosate was isolated via vacuum filtration using a 350 mL coarse glass Buchner funnel atop a 2-L vacuum flask. The resulting cake was washed with ½ cake volume of deionized water, allowed to be sucked dry for one hour using a water aspirator, then allowed to sit overnight in the chemical fume hood. The cake was placed in a vacuum oven to dry overnight at ambient temperature, transferred to a 600 mL glass vial, and then the drying process was completed overnight in the vacuum oven. This resulted in collection of 179.42 g of product and an 89.7 percent recovery (yield). Analysis of the sample showed it to contain >99.9 percent PMG by assay, with 0.04 percent glycine, 0.04 percent MePMG, and 0.06 percent glyphosine.

What is claimed is:
1. A process for the purification of glyphosate (PMG), having glycine, N-methyl-N-(phosphonomethyl)glycine or glyphosine impurities, comprising:
   1) dissolving or suspending a material comprising PMG, having glycine, N-methyl-N-(phosphonomethyl)glycine or glyphosine impurities, in water, in the presence of a base, to produce a composition comprising a PMG salt in an aqueous base,
   2) contacting the composition with an acid, such that the PMG salt is neutralized, forming a precipitate of PMG, and
   3) isolating the precipitate of PMG,
with the proviso that the composition of step 1) is not concentrated or filtered using a nanofiltration membrane.

2. The process of claim 1 wherein the amount of base is from 0.5 to 1.2 molar equivalents, based on the moles of PMG material.

3. The process of claim 1 wherein amount of acid utilized for neutralization is from 0.5 to 1.3 molar equivalents, based on the moles of PMG material.

4. The process of claim 1 wherein the base is sodium hydroxide.

5. The process of claim 1 wherein the acid is hydrochloric acid.

6. The process of claim 1 wherein the purified PMG product contains less than 0.1 wt. percent glycine, based on the total weight of the purified PMG product.

7. The process of claim 1 wherein the purified PMG product contains less than 0.1 wt. percent N-methyl-N-(phosphonomethyl)glycine, based on the total weight of the purified PMG product.

8. The process of claim 1 wherein the purified PMG product contains less than 0.2 wt. percent glyphosine, based on the total weight of the purified PMG product.

9. The process of claim 1 wherein the product of step 2) has a pH of from 0.9 to 2.9.

10. The process of claim 1 wherein the product of step 2) has a pH of from 0.9 to 1.25.

\* \* \* \* \*